US011553979B2

(12) United States Patent
Batchelor et al.

(10) Patent No.: US 11,553,979 B2
(45) Date of Patent: Jan. 17, 2023

(54) SURGICAL DEVICE HAVING AN INTEGRAL FLUID DISTRIBUTION SYSTEM (71) Applicant: GYRUS ACMI, INC., Southborough, MA (US)

(72) Inventors: Kester J. Batchelor, Mound, MN (US); Huisun Wang, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 313 days.

(21) Appl. No.: 15/908,279

(22) Filed: Feb. 28, 2018

(65) Prior Publication Data
US 2019/0262092 A1 Aug. 29, 2019

(51) Int. Cl.
A61B 18/14 (2006.01)
A61B 90/00 (2016.01)
A61B 17/295 (2006.01)
A61B 18/12 (2006.01)
A61B 18/00 (2006.01)

(52) U.S. Cl.
CPC ............ *A61B 90/08* (2016.02); *A61B 17/295* (2013.01); *A61B 18/1445* (2013.01); *A61B 2018/0063* (2013.01); *A61B 2018/00142* (2013.01); *A61B 2018/00589* (2013.01); *A61B 2018/00595* (2013.01); *A61B 2018/00601* (2013.01); *A61B 2018/00607* (2013.01); *A61B 2018/126* (2013.01); *A61B 2018/1253* (2013.01); *A61B 2018/1455* (2013.01); *A61B 2218/002* (2013.01)

(58) Field of Classification Search
CPC ... A61B 90/08; A61B 18/1445; A61B 17/295; A61B 2018/00142; A61B 2218/002; A61B 2018/1253; A61B 2018/126; A61B 2018/1455; A61B 2018/00595; A61B 2018/0063; A61B 2018/00589; A61B 2018/00607; A61B 2018/00601; A61B 18/085; A61B 2018/00005; A61B 2018/00011; A61B 2018/00029; A61B 2018/1452
USPC ......................... 606/45, 48, 50–52
See application file for complete search history.

(56) References Cited

U.S. PATENT DOCUMENTS 3,447,479 A 6/1969 Rosenberg
4,096,864 A 6/1978 Kletschka et al.
4,642,090 A 2/1987 Utrata
(Continued)

FOREIGN PATENT DOCUMENTS

EP 2604210 A1 6/2013
WO WO-2012148266 A1 * 11/2012 ............. A61B 90/70

OTHER PUBLICATIONS

Maintaining Syringe Pump Precision at Lower Cost with Lead Screws, available at http://blog.helixlinear.com/bid/261632/Maintaining-Syringe-Pump-Precision-at-Lower-Cost-with-Lead-Screws, published on May 2, 2013.
(Continued)

*Primary Examiner* — Thomas A Giuliani
(74) *Attorney, Agent, or Firm* — Schwegman Lundberg & Woessner, P.A.

(57) ABSTRACT

An electrosurgical instrument can be provided that includes a pair of opposing jaws, a channel in at least one of the opposing jaws for receiving a reciprocating blade, and a fluid distribution system in communication with the one or more fluid openings located within the channel for delivering a fluid to the jaws.

20 Claims, 3 Drawing Sheets

(56) References Cited

U.S. PATENT DOCUMENTS

| | | | |
|---|---|---|---|
| 5,454,826 A | 10/1995 | Shinsuke | |
| 5,505,707 A | 4/1996 | Manzie et al. | |
| 6,139,547 A | 10/2000 | Lontine et al. | |
| 6,290,705 B1 | 9/2001 | Chan et al. | |
| 7,070,596 B1 * | 7/2006 | Woloszko | A61B 18/1482 |
| | | | 606/41 |
| 7,931,649 B2 * | 4/2011 | Couture | A61B 18/1445 |
| | | | 606/45 |
| 8,231,574 B2 | 7/2012 | Haack et al. | |
| 8,235,993 B2 | 8/2012 | Hushka et al. | |
| 8,382,654 B2 | 2/2013 | Taylor | |
| 2003/0114850 A1 | 6/2003 | McClurken et al. | |
| 2003/0216733 A1 * | 11/2003 | McClurken | A61B 18/14 |
| | | | 606/51 |
| 2004/0019350 A1 * | 1/2004 | O'Brien | A61B 18/14 |
| | | | 606/41 |
| 2005/0107785 A1 * | 5/2005 | Dycus | A61B 18/1445 |
| | | | 606/171 |
| 2005/0113766 A1 | 5/2005 | Mottola et al. | |
| 2005/0245841 A1 | 11/2005 | Turturro et al. | |
| 2008/0234672 A1 | 9/2008 | Bastian | |
| 2009/0088744 A1 | 4/2009 | Townsend | |
| 2010/0069903 A1 * | 3/2010 | Allen, IV | A61B 17/282 |
| | | | 606/49 |
| 2010/0160905 A1 * | 6/2010 | Shadduck | A61M 25/10 |
| | | | 606/27 |
| 2011/0301604 A1 | 12/2011 | Horner et al. | |
| 2011/0306968 A1 * | 12/2011 | Beckman | A61B 18/1445 |
| | | | 606/41 |
| 2012/0071871 A1 | 3/2012 | Lue et al. | |
| 2012/0330295 A1 | 12/2012 | Manwaring et al. | |
| 2015/0080876 A1 * | 3/2015 | Worrell | A61B 18/1445 |
| | | | 606/34 |
| 2015/0080879 A1 * | 3/2015 | Trees | A61B 18/1445 |
| | | | 606/40 |
| 2017/0367753 A1 * | 12/2017 | Bjorn-Rasmussen | |
| | | | A61B 17/295 |

OTHER PUBLICATIONS

Electro Lube, Mectra Labs, http://www.electrolubesurgical.com/.
Baker, Ramadan, The effects of antistick phospholipid solution on pediatric electrocautery adenoidectomy, available at http://www.electrolubesurgical.com/wp-content/uploads/eagle_surgical_litterature.pdf, published Jan. 2012.

* cited by examiner

SURGICAL DEVICE HAVING AN INTEGRAL FLUID DISTRIBUTION SYSTEM

FIELD

The present teachings relate to forceps with a first jaw and a second jaw that are movable relative to each other and a reciprocating blade that is movable between the first jaw and the second jaw and a fluid distribution system that allows a user to apply a fluid to the jaws or the blade during a surgical procedure.

BACKGROUND

Generally, forceps may be utilized for laparoscopic surgery. The forceps may be used to control delicate movements inside a patient. These forceps may be used to grip an anatomical feature. The forceps may include a gripping assembly or a cutting assembly. The forceps may include electrical energy for use in the gripping assembly. The forceps have a pair of opposed resilient jaws that are closed against each other or a cutting blade. The jaws, the blade, or both may be powered to cut or coagulate during a surgical procedure. However, electrically powering the jaws or blade to cut tissue or a feature of interest may result in the tissue or feature of interest sticking to the jaws, blade, or both. A non-stick lubricant may be applied to the jaws, the blade, or both; however, through repeated use the lubricant may be removed from a surface and sticking may occur. Examples of some forceps or pumps to move a liquid may be found in U.S. Pat. Nos. 3,447,479 and 4,096,864 and U.S. Patent Application Publication No.: 2003/0114850; 2005/0245841; 2009/0088744; 2010/0306968; and 2011/0306968 all of which are incorporated by reference herein in their entirety for all purposes. During gripping and cutting or electrically heating of the anatomical feature such as tissue the anatomical feature may stick to the jaws or blade so that the anatomical feature cannot easily be detached from the forceps. Furthermore, repeated gripping and electrically heating or cutting of the anatomical feature may potentially damage or injure the anatomical feature requiring additional healing or treatment.

It would be attractive for the forceps to include a fluid distribution system that allows for fluid to be inserted into a desired location without removal of the forceps from a surgical site. What is needed is forceps that includes one or more fluid lines, fluid pumps, fluid openings, or a combination thereof that allow a fluid to be introduced proximate to the jaws, blade, or both from a remote location while the forceps remain within the surgical site. What is needed is a fluid distribution system that applies a lubricant to a portion of the forceps that contacts an anatomical feature before power is applied so that sticking is prevented. It would be attractive to have forceps that allow a user to selectively apply one or more fluids to a desired location so that fluids can be applied to a location of interest without removal of the forceps from the surgical site.

SUMMARY

The disclosure meets one or more of the needs by providing: An electrosurgical instrument comprising: (a) a pair of opposing jaw; (b) a channel in at least one of the opposing jaws for receiving a reciprocating blade; (c) a fluid distribution system that delivers a fluid to the jaws; wherein the fluid distribution system is in communication with one or more fluid openings located within the channel.

The present teachings provide a method comprising: (1) pumping a fluid from a fluid distribution system into a channel located within one or more jaws of an electrosurgical device; (2) reciprocating the one or more jaws, a blade, or both repeatedly so that the fluid within the channel coats the one or more jaws, the blade, or both in the fluid.

The teachings herein provide forceps that include a fluid distribution system, which allows for fluid to be inserted into a desired location without removal of the forceps from a surgical site. The teachings herein provide forceps that include one or more fluid lines, fluid pumps, fluid openings, or a combination thereof that allow a fluid to be introduced proximate to the jaws, blade, or both from a remote location while the forceps remain within the surgical site. The teachings herein provide a fluid distribution system that applies a lubricant to a portion of the forceps that contacts an anatomical feature before power is applied so that sticking is prevents. The teachings herein provide forceps that allows a user to selectively apply one or more fluids to a desired location so that fluids can be applied to a location of interest without removal of the forceps from the surgical site.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a surgical device. The surgical device may be a non-electrical device (i.e., may only provide mechanical functions such as mechanical cutting or gripping). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). When power is applied an anatomical feature may be cut, cauterized, sealed, coagulated, or a combination thereof. The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may assist in applying a therapy current to a feature of interest. The forceps may move between a first position (e.g., release position) and a second position (e.g., gripping position). The forceps may be fully closed in a full-pull position or partially closed in a partial pull position. The forceps may function to be used in surgery, for example laparoscopic surgery. The forceps may be used with or without power. Current may be passed through the forceps (e.g., a conduction plate) so that the forceps are used for electro-surgery. For example, a therapy current may be passed from one jaw to a second jaw when tissue is located between the jaws and the therapy current may coagulate blood, cauterize, cut, or a combination thereof. In another example, a therapy current may be passed from one or more of the jaws to a remote electrode (e.g., a return pad). The forceps may be comprised of parts needed to perform the recited functions and may include generally, a stylet (e.g., a tubular member, a hollow tube, or an assembly of tubes), a hand piece, one or more operable mechanisms used to actuate the stylet, one or more valves, or a combination thereof.

The hand piece may be an assembly of parts or housing structures capable of forming a hand piece structure with a cavity. The forceps may be actuated by one or more operable mechanisms. The forceps may be actuated by direct pressure being applied to one or both of the jaws so that the jaws are moved towards or away from each other (e.g., laterally moved). The forceps may be actuated by movement of a trigger. The forceps may create a sufficient gripping force so that one or more features of interest of a patient's body may be manipulated by the gripping assembly, secured by the gripping assembly, or a combination thereof. The forceps may include atraumatic tissue control that assists the forceps in gripping a feature of interest, a fluid distribution system that assists in preventing sticking of a feature of interest on the jaws, blade, or both of the forceps. The forceps may be composed of parts that may extend through a tubular member. The forceps may include a stylet. The forceps may be free of any members that extend through a tubular member. For example, the forceps may be configured as tweezers that are used in open surgery and the user may directly grasp portions of the forceps. The forceps may be an assembly of parts rotatable about an axis (e.g., a rotational axis of the forceps, the longitudinal axis of the tubular member, a longitudinal axis of the forceps, or a combination thereof). The forceps may grip and release while being simultaneously rotated. The forceps may be actuated by the actuation mechanism in communication with the forceps or a user directly contacting the forceps. The forceps may be actuated by retracting the two opposing jaws into the stylet (e.g., one or more tubular members) forcing the two opposing jaws closed. The forceps may be actuated by extending the one or more tubular members away from the hand piece (e.g., distally) so that the one or more tubular members move the two opposing jaws towards one another into a retracted position, creating a gripping force, or both. The jaws may be retracted (e.g., moved proximally into the stylet or tubular member) so that the jaws are compressed together. The forceps may generally have two or more opposing jaws, and one or more jaw shafts or legs, one or more valves, or a combination of both. Preferably, the forceps may have two jaw shafts or legs that each include an arcuate section and an opposing jaw attached to each of the jaw shafts or legs so that the forceps may be moved between a release position and a retract position when a trigger is moved relative to a hand piece.

The hand piece may function to form an enclosing structure for all or a portion of the forceps, a gripping portion for the user, a main portion for manipulating the forceps, or a combination thereof. The hand piece may be any device that houses all or a portion of the working assemblies and parts of the forceps. The hand piece may be comprised of one or more housing structures. Preferably, the hand piece is two or more housing structures. The hand piece may be any structure that is gripped by a user. The hand piece may be any structure that combines one or more of the components discussed herein so that the surgical device is formed. The hand piece may assist in performing laparoscopic surgery. The hand piece may be ergonomically shaped. The ergonomic shape of the hand piece may be any shape so that the forceps may be used ambidextrously. The ergonomic shape of the hand piece may be any shape such that all the controls can be accessed by a single hand gripping the hand piece. The hand piece may be comprised of housing structures. The housing structures may be one or more devices that form the hand piece. The housing structures may be any devices that may affix certain pieces into position. The housing structures may form a cavity to house working assemblies of the forceps. The housing structures may be one or more housing structures and preferably two or more housing structures. The housing structures may be any device that includes a recess for receiving one or more components of the forceps. The housing structures may house all or a portion of one or more operable mechanisms, one or more valves, one or more fluid distribution systems, or a combination thereof. The housing structure may house all or a portion of an operable mechanism that causes the jaws to move, the blade to move, the valve to open, the valve to close, all or a portion of a fluid distribution system, or a combination thereof. The housing structure may be made of one or more housings.

The one or more housings may function to form a hand piece, enclose a portion of an operable mechanism, a fluid distribution system, enclose a portion of a stylet, enclose one or more tubes, or a combination thereof. The one or more housings may be a left half and a right half. The housing may be multiple pieces that are connected together. The housing may be made of plastic. The housing may be a combination of plastic and metal. The housing may include a grip. The housing may be a handle that a user grips. The housing may provide a stationary part that a user grips while a user moves a trigger to actuate the forceps, a blade, or both. The housing may include one or more links (e.g., a cut lever/cut trigger or a clamp lever/clamp trigger) extending therefrom. Preferably, the housing is connected to two or more triggers that movably connect to the housing so that upon actuation the jaws, blade, fluid distribution system, or a combination thereof are moved or actuated by one of the two or more triggers. More preferably, the triggers are movable relative to the handle to actuate the jaws, blade, fluid distribution system, or a combination thereof. The housing may be free of links. The housing may be connected to a first jaw, a second jaw, or both jaws of forceps and a direct force may be applied to the housings in order to move the forceps towards or apart from each other. For example, upon a force being applied to the housing the jaws may move towards each other. In another example, upon a force being applied to the housing the jaws may move apart. The housing be a proximal end (e.g., end closest to a user) and the jaws or blade may be the distal end (e.g., end farthest from a user). However, the housing may extend from a proximal end to substantially the distal end. The jaws, blade, fluid distribution system, or a combination thereof may be moved between a first position (release position) and a second position (retract position) by one or more operable mechanism or direct contact by a user. Preferably, the jaws are movable by one or more triggers moving relative to the handle.

The one or more triggers function to be an input to an operable mechanism. The one or more triggers as discussed herein may be a lever, handle, link, or a combination thereof. The one or more triggers may be a cut trigger, a clamp trigger, fluid distribution trigger (e.g., an activation switch), or a combination thereof that when actuated inputs movement into an operable mechanism so that the operable mechanism provides an output. If the triggers are a lever, the lever is a rigid member that turns on a pivot. The cut lever, the clamp lever, or both may function to move one or more jaws, one or more blades, a jaw support rod, a blade support rod, a second link, one or more valves, or a combination thereof. The cut lever, the clamp lever, or both may extend between a release position (e.g., a start position) and a retract position (e.g., a full pull position where the jaws are closed, a valve is closed, the blade is extended, or a combination thereof). The cut lever, the clamp lever, or both as they extend from a start position to a full pull-position may close jaws, close a valve, extend a blade, or a combination thereof. For example, as the clamp trigger is moved, the clamp trigger may begin to close the jaws and as the jaws close the valve may simultaneously be closed such that an amount of fluid passing through the jaws is decreased until the jaws are closed.

The one or more operable mechanism may function to move one or more jaws, both jaws, a blade, one or more valves, one or more fluid distribution systems, or a combination thereof. The one or more operable mechanism may include a four bar mechanism, a five bar mechanism, or even a six bar mechanism. The operable mechanism may include one or more rods (e.g., a blade support rod, a jaw support rod, or both). The one or more operable mechanisms may be or include one or more levers, links, triggers, or a combination thereof. The one or more operable mechanism may include a cut lever or cut trigger (e.g., that moves a blade), a clamp lever or cut trigger (e.g., that moves the jaws between a release position and a retract position), or both. The one or more levers may be an input that a user actuates to activate the operable mechanism. The one or more levers may be part of the operable mechanism. One lever or trigger may be part of the operable mechanism and one lever or trigger may be separate from the operable mechanism. The one or more operable mechanisms may be any device that may be manipulated or moved by applying pressure or a force to a portion of the one or more operable mechanisms with a hand, finger, foot, or a combination thereof to produce an output movement on an output element or apply an output force on an output element. The one or more operable mechanisms may be any device that may connect other moveable components, for example the tubular member, a cutting assembly, a blade assembly, a functional assembly, a jaw, a jaw support rod, a valve, or a combination thereof together. The one or more operable mechanisms may be actuated ambidextrously. The one or more operable mechanisms may be a single operable mechanism that may be linked to two different functions and may be moved to generate each function simultaneously. For example, actuation of a trigger may cause gripping and cutting simultaneously. The operable mechanism may function to convert rotational movement into longitudinal movement. An operable mechanism may function to axially move one or more jaws, one or tubes (e.g., hollow tubes or solid tubes), one or more blades, or a combination thereof. The operable mechanism may include one or more tubes, support rods, or both. Each axially or rotationally moving member may be connected to an operable mechanism. Preferably, the operable mechanism causes the jaws to rotate about a pivot so that the jaws move between an open position and a closed position and the valve moves between an open position and a closed position. The one or more operable mechanisms, triggers, or both may be connected to one or more return mechanisms that assist in returning the blade, jaws, valves, or a combination thereof back to a home position when an actuation event is completed.

The return mechanism may assist in actuating the triggers (e.g., cut trigger, the clamp trigger, or both), valves, blades, jaws, or a combination thereof. The return mechanism may return the one or more triggers to a neutral position and/or a starting position (e.g., a home position) after actuation. The return mechanism may be any device that biases one or more of the links to a resting position so that when one or more of the triggers are actuated and released from actuation the tubular member, stylet, jaws, blade, valves, triggers, or a combination thereof return back to a resting position. The return mechanism may be located on a distal side or a proximal side of one or more of the triggers, activation switches, activation device, or a combination thereof. The return mechanism may be located on a distal side or a proximal side of a blade, jaws, valve, pivot, tube, or a combination thereof. Preferably, a return mechanism is located on a proximal side of one or more components of a stylet (e.g., a jaw support rod, a blade support rod, tube, or a combination thereof). The return mechanism may be and/or include a biasing member (e.g., a spring structure, an elastic member, a compressible member, a stretchable member, any structure that can be compressed and released, any structure that can store and release energy, or a combination thereof). The return mechanism may be a return spring or a compression spring. The return mechanism may be connected to a proximal end of a stylet, a tubular member, a link of a four bar mechanism (e.g., a first link, a second link, a third link, a fourth link), an operable mechanism, or a combination thereof. The return mechanism may assist in moving a first link from a first position to a second position so that the jaws (e.g., forceps) of the electrosurgical device are moved between a closed position and an open position, a valve is moved between a closed position and an open position, or both. Preferably, the return mechanism assists in moving one or more jaws of forceps (e.g., two opposing jaws).

The two or more opposing jaws may function to create a gripping force. The two or more opposing jaws may move towards each other to create a gripping force, to grip a feature of interest, or both. The two or more opposing jaws may be any device that may be used to grip items of interest in surgery, for example laparoscopic surgery. The two or more opposing jaws may function to be used to grip or clamp an item of interest for cutting or applying a bipolar energy source. The two or more opposing jaws may be any shape and size so that the jaws perform a gripping function, create a gripping force, or both. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The two opposing jaws may be one solid piece. Each of the two opposing jaws may be substantially sold and may include one or more fluid openings, one or more conduction plates, one or more teeth, mesh, channels, or a combination thereof. The two opposing jaws may be formed of two wires that are shaped to have a generally "U" shaped end. The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The two opposing jaws may be made of a material that conducts electricity. The two opposing jaws may include a channel (e.g., a blade track) to allow for a cutting instrument to be inserted while retaining functionality of the two or more opposing jaws.

The two opposing jaws may be used to apply electricity to a feature of interest that may be gripped by the two opposing jaws. The two opposing jaws may be a first jaw and a second jaw. The first jaw may be movable relative to the second jaw, or vice versa. The first jaw and second jaw may be longitudinally movable relative to each other. Preferably, the first jaw and second jaw longitudinally move in unison. The first jaw and second jaw may be longitudinally static. The first jaw and second jaw may move about a pivot towards and away from each other. The first jaw, the second jaw, or both may laterally move relative to each other (i.e., linearly directly towards and away from each other). The gripping portion of the two opposing jaws may have a surface texture to grip a feature of interest (e.g., teeth or mesh). For instance the surface texture may be smooth, flat, contoured, serrated, textured, include ridges, mouse teeth, or a combination thereof. Preferably, the gripping portion of the two opposing jaws may have a serrated edge to allow for more secure gripping. The two opposing jaws may have an edge with a surface that may function similar to a serrated edge to allow for secure gripping. The two opposing jaws may be moved between a release position and a retract position by retraction of one of the one or more jaw shafts, movement of the one or more tubular members towards the distal end, or both along an axis of the one or more tubular members; an application of force by a user; or a combination thereof. The two opposing jaws may include a jaw bias mechanism, be part of an operable mechanism, or both. The two opposing jaws may have laterally extending arcuate sections at the proximal end (e.g., heel of the jaw) of the jaws that protrude out from the distal end of the tubular member, while one or more jaw support rods extend into the tubular member. The two or more jaws may rotate above a pivot to open and close and the jaw support rods move.

The one or more pivots may function to connect a first jaw and a second jaw together. The one or more pivots may function to create a point that the first jaw and the second jaw move about between an open position and a closed position. The one or more pivots may be a pin. The one or more pivots may be a movable connection location between two or more jaws. Each jaw may include one or more holes or recesses that receive a connection device (e.g., a pin) that movably connects the jaws together. The one or more pivots may function to assist in opening and closing the valves. Each jaw may include a pivot that allows the jaws to rotate towards each other and allow each of the jaws to move between an open position and a closed position. The pivots may close jaws, open jaws, close valves, open valves, or a combination thereof. The one or more pivots may assist in activating and deactivating a fluid distribution system. The one or more jaws may be moved about the pivot by the one or more jaw support rods moving axially within a neck or a stylet, between the jaws, or both.

The one or more jaw support rods may function to assist a user in aligning a feature of interest between two or more opposing jaws, assist in creating a gripping force between the two opposing jaws, provide support to one or more jaws, extend through one or more tubular members and/or tubular members, or any combination thereof. The one or more jaw support rods may be a leg, a jaw shaft, or both. The one or more jaw support rods may extend through a central portion of the tubular member (e.g., a neck) and the one or more jaw support rods are movable relative (i.e., parallel, axially, or both) to the tubes. The jaw support rods may be generally any shape that will perform the recited functions. The jaw support rods may be any light weight material that is strong enough to support the two opposing jaws and to support the gripping action of the jaws. The one or more jaw support rods may have a cross-section that is a solid cylindrical rod, a hollow cylindrical rod, a half circle shape, or a combination thereof. The jaw support rods may include one or more flat portions, may include non-arcuate portions, may be asymmetrical, or a combination thereof. The jaw support rods may be flexible, rigid, conductive, elastically deformable, or a combination thereof. Preferably, the one or more jaw support rods may form the jaw and fold back upon itself to form an opposing leg of the jaw. For example, the jaw support rods may extend out of the tube and curve back into the tubular member so that the portion extending out of the tubular member forms the jaws. The one or more jaw support rods may extend through and out the tubular member at the distal end of the tubular member, at the proximal end of the tubular member, or a both. The one or more jaw support rods may extend out of the distal end of the tubular member and may have a functional attachment connected to the distal end of the one or more jaw support rods. The functional attachment may be connected to one or both of two opposing jaws or an attachment with the functional equivalent of performing a gripping function. The one or more jaw support rods may be adjacent to, extend along opposing sides, surround, or a combination thereof the cutting assembly inside the tubular member. The one or more jaw support rods may terminate in a distal end region of the tubular member, an inner tube, or both. The surgical device may be free of jaw support rods, blade support rods, or both. For example, when the surgical device is configured for open surgery the jaws may be exposed at all times and may be free of jaw support rods that assist in closing or opening the jaws. The one or more jaw support rods may include or be connected to one or more bias mechanisms. The one or more jaw support rods, the bias mechanisms, or both may close the jaws, move the blade, or both so that a conduction plate of the jaws provide power to a feature of interest.

The conduction plate functions to transfer power, heat, cool, or a combination thereof from the jaws of the surgical device to a feature of interest (e.g., tissue, veins). The conduction plates may both conduct power to a feature of interest and assist in gripping a feature of interest. The conduction plate may be attached to the jaws and may conduct power through the jaws. The conduction plate may be connected to a portion of the jaws that has insulative properties (e.g., a protective cover). The conduction plate may be in communication with one or more wires so that the conduction plate may provide power, heat, or both to a feature of interest. The conduction plate may be made of metal and may be connected to a plastic piece, ceramic piece, or both. The conduction plate may be made of steel, iron, a surgical steel, or a combination thereof. The conduction plate may include a non-stick coating (e.g., polytetrafluoroethylene (Teflon®)). The conduction plate may extend around an outer perimeter, an inner perimeter, or both of the jaws. The conduction plate may be a solid plate that is one piece. The conduction plate may be a plurality of conductive pieces that are individually connected to the jaws. The conduction plate may be a mesh. The conduction plate or mesh may be one or more wires. The conduction plate or mesh may be a plurality of interwoven wires. The conduction plate or mesh may be wires that are crisscrossed together to provide gripping portions with fluid openings between the gripping portions. The mesh may create a gripping surface similar to teeth. The mesh may be provided on the face of the jaws instead of teeth.

The face may function to be a contact surface of each of the jaws. The face may contact the feature of interest and assist in holding the feature of interest in place. The face may be smooth, include teeth, include mesh, include a conduction plate, include one or more of the fluid openings, or a combination thereof. Preferably, the face contacts a feature of interest and assists in retaining the feature therein so that a feature of interest is retained between the jaws. The face may be made of metal, plastic, a conductive material, an insulating material, a smooth material, a rough material, a material that will not damage an anatomical feature, steel, iron, nickel, stainless steel, copper, silver, silver coated, steel coated, or a combination thereof. A fluid, lubricant, or both may be applied to the face before, during, or after a therapy current is applied through the face. More preferably, the lubricant may be added to the face while the face is located within a surgical site. Preferably, at least a portion of the face may be a conduction plate that assists in conducting power from the surgical device to a feature of interest. The face may include one or more teeth to assist in holding a feature of interest.

The teeth may function to assist in holding a feature of interest between two jaws. The teeth may function to prevent the feature of interest from being removed from between two jaws. The teeth may be "V" shaped, rectangular, square, oval, or a combination thereof. The teeth may be free of sharp edges (e.g., two or more sides that converge to create a point or line). The teeth may include sharp edges. The teeth may create a peak so that a portion of a feature of interest may extend between the peaks into the valleys so that the feature of interest is retained between the jaws, so that the feature of interest is prevented from being removed from the jaws, or both. The teeth may be an extension of the conduction plate. The teeth may be located in an alternating fashion with the fluid openings. The teeth may include one or more fluid openings. The teeth may assist in holding the feature of interest in place as the jaws move from an open position to a closed position. The teeth may work in conjunction with the fluid openings so that the feature of interest is retained between the jaws. The teeth, fluid openings, or both may assist in preventing a feature of interest from being removed from between the jaws when a cutting assembly is being used to cut the feature of interest.

The one or more fluid openings may function to allow fluid to pass into the jaws, out of the jaws, through the jaws, onto the blade, or a combination thereof. The one or more fluid openings may be located on a portion of a jaw that faces another jaw (e.g., a face of the jaw). The one or more fluid openings may be a hole within the conduction plate, face, teeth, contact surface, or a combination thereof. The one or more fluid openings may permit fluids to extend into or out of the jaws. Preferably, the one or more fluid openings permit a liquid to extend into or out of the jaws. More preferably, the fluid openings allow for a liquid to move outward and into contact with the jaws, the blade, or both. The fluid openings may assist in equally distributing a liquid onto a contact surface (e.g., face) of the jaws, the blade, or both. The fluid openings may have any shape so that fluid may be moved thorough the fluid openings to assist in lubricating one or more contact surfaces of a blade, a jaw, or both. The fluid openings may be square, round, oval, rectangular, diamond, "U" shaped, half "U" shaped, linear, arcuate, two or more parallel openings, or a combination thereof. The fluid openings may have a constant cross-sectional thickness from an entrance to an exit of the fluid openings. The fluid openings may have a cross-sectional thickness that decreases as the fluid openings extend from the entrance to the exit of the fluid openings (e.g., may be cone shaped if the fluid openings are circular). The fluid openings may be located in a face, in a conduction plate, a mesh, teeth, between teeth, in a channel, or a combination thereof. The one or more fluid openings may allow fluid to be moved into the fluid openings and then distributed about the blade, the jaws, or both. The fluid openings may extend through a face of each of the jaws, the blade, or both. The one or more fluid openings may be located within a channel, near a channel, or may provide a fluid into the channel so that as a blade moves within the channel the fluid is transferred to the blade.

The one or more channels may be any shape and size so that a blade, functional element, a surgical instrument, or a combination thereof may be extended into the channel in the jaws, into the channel between the jaws, or both. The blade, a surgical instrument, functional element, or a combination thereof may be extended into the channel formed in (or between) the two opposing jaws while the two opposing jaws are closed, open, or in a position therebetween. The channel may allow the blade to extend out of the jaws while the jaws were closed. The channel may lock the blade in place when the jaws are closed. The channel may fill with a fluid and preferably a lubricant as the blade is advanced through the channel. The channel may be formed in the opposing jaws, the jaws may be made of a wire material that may be formed to include the gap, material may be removed to form the gap, or a combination thereof. The channel (e.g., blade track) may extend along the longitudinal axis of the tubular member, blade, or both so that the blade axially extends into the channel during use. The material the jaws are made of may be formed to include a channel. The channel may be an absence of material in one or both of the jaws. The channel may extend through substantially the center of each jaw so that the jaws are generally "U" or "C" shaped. The channel may include one or more fluid openings. The channel may allow the blade to extend between the jaws such that the blade is perpendicular to a face of the jaws. The channel may receive or be filled with a fluid, a lubricant, or both so that as the blade, cutting assembly, or both extends through the channel the blade is coated with a fluid, lubricant, or both.

The cutting assembly may be any assembly of parts capable of cutting. The cutting assembly may function to cut tissue, veins, arteries, an anatomical feature, a feature of interest, or a combination thereof during a surgical procedure. The cutting assembly may be any cutting assembly that may be used in surgery, for example laparoscopic surgery or open surgery. The cutting assembly may be an assembly of parts that may fit inside the tubular member and/or tube, extend through the stylet and/or tubular member, extend between the pair of opposing jaws, extend between legs, extend between legs and jaws, extend between jaw support rods, extend between jaws, extend into a channel, or a combination thereof. The cutting assembly may be any assembly of parts capable of rotating independent of the tubular member or in combination with the tubular member. The cutting assembly may be actuated to perform a cutting function by an operable mechanism. The cutting assembly may be any cutting assembly that may generally be comprised of a blade, a blade shaft, or a combination thereof.

The blade may function to cut a feature of interest. The blade may be any cutting tool that may be used in surgery, for example laparoscopic surgery or open surgery. The blade may be any cutting device that may be extended and retracted through the tubular member. The blade may extend along a stylet. The blade may be made of any material that may be sharpened; is strong enough to cut a feature of interest; is biocompatible; that may conduct electricity; or a combination thereof. The blade may mechanically cut, electrically cut, or both. The blade may be any shape so that the blade may fit inside the tubular member and extend into the channel formed between the two opposing jaws, between two legs connected to a jaw, or both so that a feature of interest may be cut. The blade may be substantially solid along its length. The blade may have a length so that the blade is sufficiently long to cut a feature of interest. The maximum length of the blade may be equal to the length of the jaws. The length of the blade may be substantially equal to that of the protrusions of the camming shaft. The length of the blade may be less than that of the protrusions. The blade may include one or more recesses. The blade may be sufficiently small so that the blade may be housed in the tubular member, tube, or both of a stylet during movement, insertion, or both. The blade may be extended into, and retracted from, the channel in the two opposing jaws. The distal end of the blade may have a shaped edge. The blade may extend flush with or distal of the jaws. The blade may conduct power. The blade may conduct a therapy current. The blade may conduct bipolar energy, monopolar energy, or both. The proximal end of the blade may be attached to a blade support rod.

The blade support rod may function to support the blade and assist in moving the blade axially. The blade support rod may extend the blade axially along the axis of the tubular member, the stylet, or both and out of the tubular member, stylet, or both (e.g., into the channel formed by the two opposing jaws). The blade support rod may move the blade axially upon movement of the operable mechanism, the operable mechanism, the first link, or a combination thereof. The blade support rod may function to extend and/or retract the blade via an operable mechanism. The blade support rod may be used to actuate a blade during surgery. The blade support rod may be of any shape and size to actuate a blade inside a tubular member. For example the blade support rod may be a wire, shaped metal, a rod, a plurality of combined longitudinal pieces, or any similar rigid structure that may fit in and extend through the tubular member. The blade support rod may be connected to a trigger, a slider, or both. The blade support rod may be made of a material that is lightweight, but strong enough to extend a blade through a feature of interest thereby cutting the feature of interest. The blade support rod has a distal end and a proximal end. A blade may be attached to a distal end, a distal end region, or both of the blade support rod. The blade support rod may extend through, around, along, next to, parallel to, or a combination thereof a pivot that connects the first jaw, and the second jaw together. The blade support rods may extend through a stylet (e.g., neck) that connects the blade to a hand piece.

The stylet as discussed herein may include one or more tubular members or may be the tubular member (i.e., tube). The stylet may form a neck that extends between a distal end and a proximal end. The stylet may be a neck that connects jaws, a blade, or both to a hand piece. The stylet may have a hollow cross-section, a solid cross-section, or both. The stylet may include one or more tubes and one or more shafts may extend through the tubes. For example, an inner tube may be solid and an outer tube may be hollow. The stylet may include a tubular member and an inner tube. The stylet may include a tube that extends around all or a portion of an inner tube. The stylet may be a hollow tube with one or more shafts extending through the hollow tube. The stylet may function to extend into a patient during a surgical procedure so that a user (i.e., surgeon) can perform one or more surgical procedures. The stylet may be flexible so that the stylet may be moved within a patient. Preferably, the stylet may be substantially rigid so that the stylet may be moved to a desired location. The stylet includes a distal end and a proximal end. The distal end may be an end of the stylet that is located farthest from the hand piece (e.g., the end of the stylet that is inserted into a patient). The proximal end of the stylet may be the end of the tube located proximate to the user, in the hand piece, or both. For example, the proximal end may extend into the hand piece so that manipulation of the one or more operable mechanisms manipulates the tube. The stylet and its components may be made of any biocompatible material, for example, stainless steel, plastic, a synthetic material, a natural material, or a combination thereof. The stylet may comprise a tube sub-assembly. The stylet may carry a fluid from a proximal end to a distal end. The stylet may include one or more fluid lines that carry a fluid from a proximal end to a distal end. Preferably, the stylet carries a lubricant from a proximal end to a distal end. The tube sub-assembly may include one or more tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, one or more valves, one or more jaw shafts, one or more blade shafts, or a combination thereof.

The one or more outer tubes may function to close the jaws, bias the jaws, or both. The one or more outer tubes may function to house one or more jaws, one or more blades, or both. The one or more outer tubes may be axially static. The one or more outer tubes may axially move to open and close the jaws. The one or more tubes may house a valve or be in communication with a valve. The one or more outer tubes may house one or more fluid lines. One or more fluid lines may extend from a proximal end to a distal end of the outer tube. The one or more tubes may function to bias the actuation mechanisms that bias the jaws. The one or more tubes may function to protect the inner tube. The one or more jaws may move relative to the inner tube. The one or more jaws may axially move towards the distal end and the proximal end during movement. Preferably, the one or more outer tubes may be hollow. The one or more jaws may overrun the inner tube, the jaws, the arcuate sections, or a combination thereof to bias the jaws towards each other. The one or more inner tubes may function to create a point of contact for one or more jaws. The one or more inner tubes may function to connect to a camming shaft. The one or more inner tubes may function to extend through all or a portion of the stylet. The one or more inner tubes may form a connection point, include a connection feature (e.g., a pin, bolt, screw, rivet, or a combination thereof) for one or more jaws. The one or more inner tubes may connect to a pivot joint of one or more jaws so that the one or more jaws rotate about an axis. The one or more inner tubes may assist in opening and closing the jaws, valves, or both. The one or more inner tubes may be located distal of one or more tubes. The one or more inner tubes may be part of a tubular member or a stylet. The one or more inner tubes may be movable relative to an outer tube. The one or more inner tubes may be axially movable, rotationally movable, or both relative to an outer tube, a camming shaft, or both. The one or more inner tubes may be static and an outer tube may be movable relative to the inner tube. The one or more inner tubes may be substantially the same length as an outer tube. The one or more inner tubes may be shorter than an outer tube. The one or more inner tubes may be in communication with a camming shaft. The one or more inner tubes may be hollow. The one or more inner tubes may be solid. The one or more forceps may be free of any tubes or tubular members. The one or more inner tubes, outer tubes, stylets, or a combination thereof may form part of a fluid distribution system, connect a fluid distribution system between a jaw, blade, or both and a hand piece.

The fluid distribution system functions to provide a fluid to a location of an electrosurgical device and preferably to a blade or jaws of an electrosurgical device while the electrosurgical device is located within a surgical site without having to remove the electrosurgical device from the surgical site. The fluid distribution system may move a fluid from a proximal end to a distal end of the electrosurgical device. The fluid distribution system may move a lubricant into contact with the blade, the jaws, or both. The fluid distribution system may extend between a fluid pump and one or more fluid openings. The fluid distribution system may include one or more fluid lines, one or more fluid pumps, one or more engagement switches, one or more fluid reservoirs, one or more refill ports, one or more activation devices, one or more motors, one or more cams, one or more fluid openings, a quantity of lubricant, or a combination thereof. Preferably, the fluid distribution system includes at least one fluid line that transports a fluid from a reservoir or pump to a distal end of an electrosurgical device.

The one or more fluid lines may connect one or more fluid openings with a fluid pump, a fluid reservoir, or both. The one or more fluid lines may extend through a neck, a stylet, one or more tubes, or a combination thereof. The one or more fluid lines may be a tube that extends between a distal end and a proximal end of the electrosurgical device, surgical device, or both. The one or more fluid lines may be a cannula that is formed in a tube and the cannula may carry a fluid through the electrosurgical device. The one or more fluid lines may terminate at the distal end and directly apply a fluid to a location of interest. The fluid lines may expel a fluid into a channel, on a jaw, on a blade, or a combination thereof. The fluid lines may extend from a pump, a reservoir, or both through a neck or stylet, and to a location of interest such as a jaw or blade. The one or more fluid lines may be free of a valve. The fluid lines may include one or more valves to control the flow of fluid.

The one or more valves may function to control a flow of fluid through to a distal location, the jaws, the blade, or a combination thereof. The one or more valves may permit fluid to flow when the electrosurgical device is electrically activated. The one or more valves may prevent fluid from flowing when the electrosurgical device is electrically deactivated. The one or more valves may prevent fluids from moving from a distal end towards a proximal end. The one or more valves may prevent a fluid from heading towards the pump, reservoir, or both. The one or more valves may be a check valve. The one or more valves may permit fluid to pass when a fluid pump is activated, a motor is turned on, power is supplied, the electrosurgical device is electrically activated, or a combination thereof. The one or more valves may be opened for a duration of time before the electrosurgical device is activated. The one or more valves may be opened when the pump is activated. The one or more valves may only open when the fluid pump is opened. The one or more valves may split fluid between two or more fluid lines, three or more fluid lines, or a plurality of fluid lines so that fluid is distributed between a plurality of fluid openings. The one or more valves may meter a predetermined amount of fluid to a desired location. The one or more valves may only be opened when a fluid pump is activated.

The one or more fluid pumps (i.e., pump) may function to move a fluid from a proximal end to a distal end. The one or more fluid pumps may move a fluid from a hand piece to a blade, a jaw, or both. The one or more fluid pumps may be a syringe, a reservoir and plunger, a rotary pump, a hand pump, a bulb pump, a positive displacement pump, plunger pump, piston pump, diaphragm pump, a peristaltic pump, or a combination thereof. The one or more fluid pumps may be connected to a motor. The one or more fluid pumps may be free of a connection to a motor. The one or more fluid pumps may be manually operated. The one or more fluid pumps may be entirely located within a hand piece. The one or more fluid pumps may be located partially inside of the surgical device and partially located outside of the surgical device. The fluid pump may create pressure. The fluid pump may move a fluid from a reservoir to a desired location. The fluid pump may be electrically or manually activated upon actuation of an engagement switch.

The one or more engagement switches may function to cause a fluid to be moved by the fluid pump. The one or more engagement switches may activate a motor, a pump, or both. The one or more engagement switches may directly move a portion of the pump (e.g., an actuation device, a cam, an activation switch, or a combination thereof). The one or more engagement switches may be a portion of the pump that is externally actuated to activate a pump. The one or more engagement switches may be an on off button. The one or more engagement switches may turn a motor on or off. The one or more engagement switches may be activated by contact with one or more activation switches. The one or more engagement switches may be located inside of a hand piece. The one or more activation switches may move to create a fluid force. The one or more engagement switches may be a plunger that forces a fluid from a fluid pump, a fluid reservoir, or both. The one or more engagement switches may move to force fluid from a reservoir into the fluid line. The one or more engagement switches may deactivate as soon as an application of force is stopped, as soon as contact is ceased with the activation switch, or both. Preferably, the engagement switch extends into contact with or into a reservoir to move a fluid through the fluid distribution system.

The fluid reservoir functions to contain a sufficient amount of fluid so that the fluid may be applied to a desired location during a surgical procedure. The fluid reservoir may contain a sufficient amount of fluid for one surgical procedure without requiring refiling. The fluid reservoir may hold enough fluid for one or more applications, two or more applications, three or more applications, or a plurality of applications before refilling is needed. The fluid reservoir may hold one or more types of fluid. Preferably, the fluid reservoir holds a lubricant as discussed herein. The fluid reservoir may be solid or made of solid material. The fluid reservoir may be pliable, elastic, resilient, compressible, or a combination thereof. The reservoir may act both as a pump and a reservoir. The reservoir may be ball shaped and upon depression of the reservoir the reservoir may expel a fluid. The fluid distribution system may be free of a reservoir. The reservoir may be manually activated to cause movement of the fluid into and through the fluid line. The reservoir may be split into one or more chambers, two or more chambers, or even three or more chambers. The chambers of the fluid reservoir may include a refill port so that additional fluid or a different fluid may be inserted into the fluid reservoir during use.

The refill port may function to permit additional fluid or new fluid to be introduced into the electrosurgical device while the electrosurgical device is being used, is partially located within a surgical site. The refill port may form a sealed connection with the reservoir so that the reservoir is not contaminated. The refill port may include a threaded connection, a membrane, a rubber material, an openable and closeable top, or a combination thereof. The refill port may permit a needle of a syringe to penetrate into the reservoir so that the reservoir may be refilled. The refill port may seal after being filing so that the refill port cannot be reused. The refill port may extend through a wall of the hand piece to a location proximate to the fluid reservoir or connected to the fluid reservoir so that fluid may be added to the reservoir. Each chamber of the reservoir may include one or more refill ports. Each of the refill ports may receive one or more fluids.

The one or more fluids may function to assist a surgeon in performing a procedure, to minimize trauma to a patient, to deliver a drug, deliver a therapy fluid, deliver a lubricant, or a combination thereof. The one or more fluids may be a gas. Preferably, the one or more fluids are a liquid. The one or more fluids may be an antibiotic, a steroid, or both. The one or more fluids may prevent tissue from sticking to a blade, an electrode, a jaw, or a combination thereof when the blade, the jaw, or both are used mechanically, electrically, or both. The one or more fluids may assist in conducting electricity. The one or more fluids may be electrically conductive. Preferably, the one or more fluids may be lubricant. One example of a preferred fluid is Electro Lube created by Mectra Labs of Bloomfield, Ind. The lubricant may an anti-stick solution. The lubricant may be an organic based substance. The lubricant may be bio-compatible. The lubricant may be a lecithin based phospholipid mixture derived from soybean oil. The lubricant may prevent tissue from sticking to the forceps, jaws, blade, or a combination thereof during application of power, electro surgery, or both. The one or more fluids may flow from a reservoir to a blade, a jaw, a distal end, or a combination thereof. The one or more fluids may flow from a hand piece along the stylet and out to the blade, jaws, or both. The lubricant may be moved from the pump, from the reservoir, through a fluid line, to a location of interest upon an activation device creating an activation function.

The one or more activation devices may function to move a fluid to a desired location. The one or more activation devices may activate a motor. The one or more activation devices may manually activate a pump. The one or more activation devices may depress a pump. The one or more activation devices may axially move a plunger, an engagement switch, or both. The one or more activation devices may meter a predetermined amount of fluid from the pump, the reservoir, or both to a desired location. The one or more activation devices may be a rotary to linear converter. For example, upon rotation of the activation device, the activation device may move along an axis or longitudinally move. The one or more activation devices may be threaded, include detents, be smooth, be an activation button, or a combination thereof. The one or more activation devices may act on the pump, the reservoir, or both. The activation devices may assist a user in manually activating the pump. The activation device may convert the reservoir into a pump. For example, when the activation device is depressed fluid may be expelled from the reservoir. The activation device may be used with the reservoir instead of using a motor, a pump, or both.

The motor may function to move a fluid from the pump, the reservoir, or both to a location of interest. The motor may be electrically powered. The motor may move the pump so that fluid is moved to a location of interest. The motor may rotate a cam, a mounting portion, an activation device, or a combination thereof. The motor may move an engagement switch, compress the fluid line, compress the reservoir, or a combination thereof to move a fluid. The motor may rotate or move an impeller, propeller, a piston, a vane, a screw, a gear, a plunger, or a combination thereof. The motor may create motion by converting electricity into kinetic energy. The motor may create fluid movement upon actuation of an activation switch. The motor may move a cam upon the motor being activated.

The one or more cams may function to actuate a pump so that fluid is moved. The one or more cams may generate pressure to move a fluid. The one or more cams may move one or more engagement switches so that the one or more engagement switches move a fluid. The one or more cams may move the engagement switch so that a predetermined amount of fluid is expelled. The one or more cams may rotate and as the cams rotate the fluid may be moved from the reservoir, the pump, or both. The one or more cams may increase in cross-sectional length as the one or more cams move so that an engagement switch is axially moved. The one or more cams may have an eccentric rotation. The one or more cams may depress a plunger as the cam rotates. For example, as the cam rotates the cross-sectional length may increase so that a plunger is axially moved. The one or more cams may rotate about a pivot point. The one or more cams may move in a direction from the proximal end to the distal end. The one or more cams may rotate about an axis and a change in cross-sectional thickness (e.g., diameter) may cause movement of the fluid. The one or more cams may be connected to an a mounting portion that assists in axially or rotationally moving the cam, the activation device, or both axially, as the cam, the activation device, or both are moved by a user, a motor, or both.

The mounting portion may function to connect a portion of the fluid distribution system to the electrosurgical device, the surgical device, or both. The mounting portion may be located within the hand piece. The mounting portion may be located inside of the hand piece. The mounting portion may be located external of the hand piece. The mounting portion may be connected an activation device, a cam, the motor, a pump, or a combination thereof. The mounting portion may be threaded so that upon movement of the engagement switch fluid is moved. The mounting portion may be threaded so that upon rotational movement of an engagement switch, an activation device, or both fluid is moved. The mounting portions may include recesses and positive portions and the positive portions may assist in moving an activation device upon contact with the positive portions. The mounting portion may assist is converting rotational movement is linear movement or axial movement. The mounting portion may be connected to or in communication with an activation device.

The activation device may function to move fluid upon an action by a user. The activation device may function to turn on a motor that causes movement of a fluid. The activation device may manually move fluid. The activation device may convert rotational movement to linear movement. The activation device may slide along a mounting portion. The activation device may turn on a motor, manually actuate the pump, the fluid reservoir, or both. The activation device may extend out of the hand piece so that the activation switch may be directly acted upon by the user. The activation device may include a portion within the hand piece and a portion located external to the hand piece. The activation device may be depressed (i.e., directly axially moved), rotated, or both. The activation device may be acted upon directly by a user, by an activation switch, or both.

The activation switch may function to move fluid. The activation switch may turn the fluid distribution system on or turn the fluid distribution system off. The activation switch may move a predetermined amount of fluid. For example, upon depressing the activation switch the motor, pump, or both may run for a predetermined amount of time so that a predetermined amount of fluid is expelled. In another example, depressing the activation switch may cause displacement of a predetermined amount of fluid so that the predetermined amount of fluid is moved. The activation switch may be an on/off switch. The activation switch may be an elastomeric switch that moves fluid. The activation switch may be connected to a printed circuit board, a power supply, one or more wires, or a combination thereof.

The power supply may function to power the electrosurgical device, the pump, the motor, the forceps, the valve, the fluid distribution system, or a combination thereof. The power supply may be connected to the electrosurgical device via a generator. The power supply may be alternating current (AC) or direct current (DC). The power supply may be portion of a generator and/or the generator may include a power supply. The generator may be connected to a power source and the generator may provide a supply of power to the electrosurgical device. The power supply may be provided to the electrosurgical device via one or more wires.

The one or more wires may function to connect the electrical surgical device, the motor, the pump, the fluid distribution system, or a combination thereof to the generator, a power source, or both. The one or more wires may extend from a generator to the surgical device to provide power, signals, or both. The one or more wires may connect the fluid distribution system to the electrosurgical device. The one or more wires may power the motor, a pump, or both so that fluid is transferred from the reservoir to a location of interest.

Figure 1:
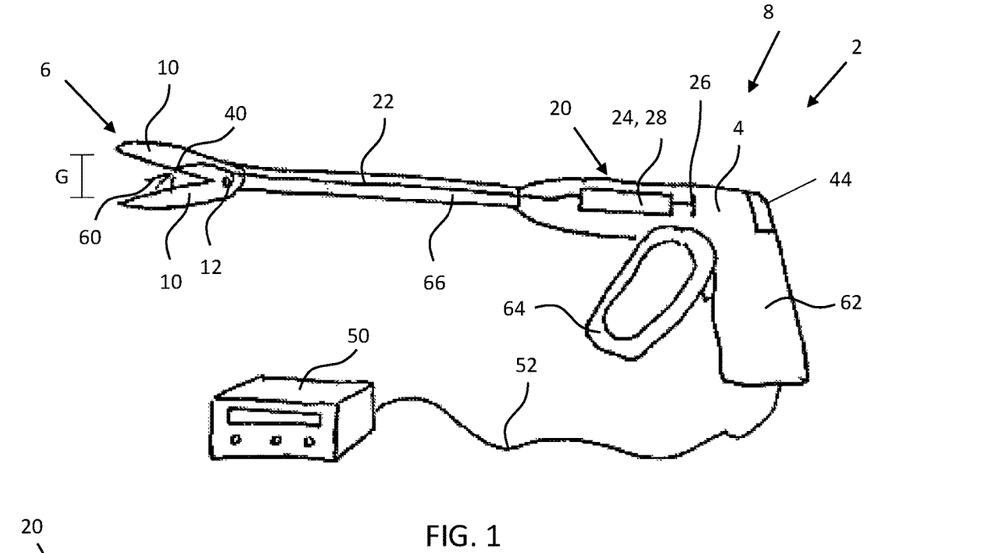
FIG. 1 is a perspective view of an electrosurgical device having a fluid distribution system.

FIG. 1 illustrates a perspective view of an electrosurgical device 2. The electrosurgical device 2 includes a surgical device 4 that as shown are configured as forceps 6 including to a plurality of jaws 10 that are connected to a handpiece 8 via a neck 66. The jaws 10 are pivotally engaged about a pivot 12 so that the jaws 10 may open and close by increasing or decreasing a gap (G) between the jaws 10. A fluid distribution system 20 is located in the surgical device 4 to distribute a lubricant 60 through a fluid line 22 and out of a fluid opening 40 to lubricate one or more conduction plates located on the jaws 10 (see FIG. 7). The fluid distribution system 20 is activated by an engagement switch 26. When the engagement switch 26 is engaged, fluid within a fluid pump 24, which is also a fluid reservoir 28, is pumped into the fluid line 22 and travels through the neck 66 (e.g., a stylet) of the electrosurgical device 2 before exiting the fluid opening 40 located on the jaw 10. The fluid distribution system 20 may be activated manually or the fluid pump 24 may be actuated by a user pressing an activation switch 44. Alternatively, the fluid distribution system 20 may be activated by engaging a trigger 64 of the surgical device 4 so that an electrical signal sent from a power supply/generator 50 through a wire 52 connected to a handle 62 of the surgical device 4 powers the engagement switch 26. The power supply/generator 50 may power the fluid distribution system 20, one or more jaws 10, or both.

Figure 2:
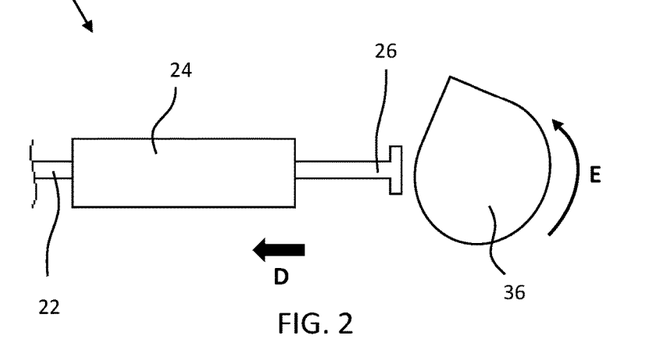
FIG. 2 is a close-up side view of a cam driven fluid distribution system.
Figure 3:
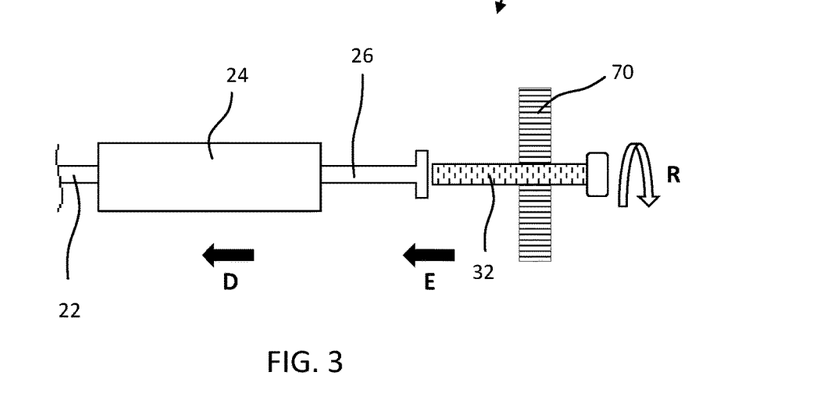
FIG. 3 is a close-up side view of a fluid distribution system having an activation device.

FIGS. 2 and 3 illustrate close-up views of a fluid distribution system 20. The fluid distribution system 20 includes a fluid pump 24 that is activated by an engagement switch 26 so that a lubricant is distributed through a fluid line 22 to lubricate one or more jaws of an electrosurgical device (see FIG. 1). As shown in FIG. 2, the engagement switch 26 is engaged when a cam 36 is rotated in an engagement direction (E) to contact the engagement switch 26. Once the engagement switch 26 is engaged, the lubricant is distributed from the fluid pump 24 through the fluid line 22 in the direction (D).

Alternatively, as shown in FIG. 3, the engagement switch 26 is engaged by an activation device 32 secured in a mounting portion 70 adjacent to the engagement switch 26. To engage the engagement switch 26, the activation device 32 is rotated in a direction (R) so that the activation device 32 travels through the mounting portion 70 in an engagement direction (E) to contact the engagement switch 26. Once the engagement switch 26 is engaged, the lubricant is distributed from the fluid pump 24 through the fluid line 22 in the direction (D).

Figure 4:
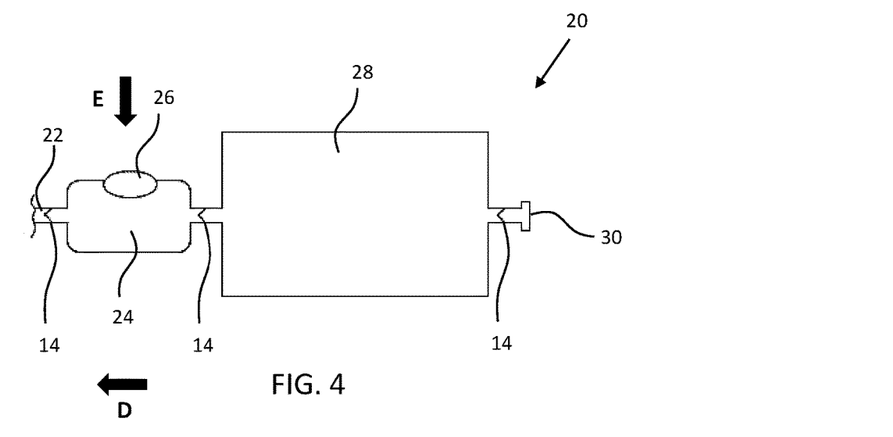
FIG. 4 is a close-up side view of a fluid distribution system having a fluid reservoir.

FIG. 4 illustrates a close-up side view of a fluid distribution system 20. The fluid distribution system 20 includes a fluid pump 24 that is activated by an engagement switch 26 so that a lubricant is distributed through a fluid line 22 to lubricate one or more jaws of an electrosurgical device (see FIG. 1). When the engagement switch 26 is compressed in an engagement direction (E), lubricant located in the fluid pump 24 exits a valve 14, and is distributed through the fluid line 22 in the direction (D). When the engagement switch 26 is released, a suction force is created so that lubricant in an adjacent fluid reservoir 28 passes through an additional valve 14 to be stored in the fluid pump 24 until the engagement switch 26 is engaged again. The fluid reservoir 28 may be refilled via a refill port 30 such that lubricant entering the fluid reservoir 28 is prevented from backflow in a direction opposing the fluid direction (D) by a third valve 14.

Figure 5:
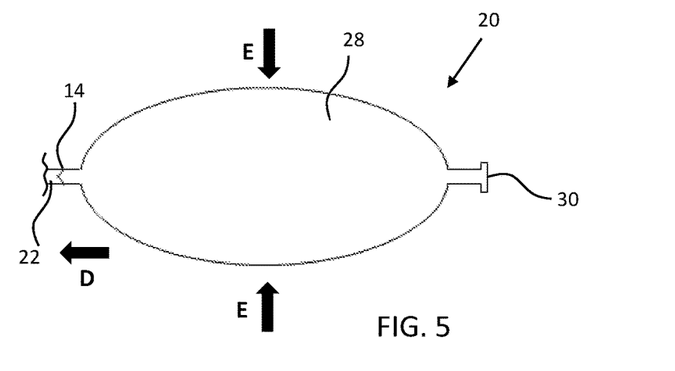
FIG. 5 is a close-up side view of a fluid distribution system having a compressible fluid reservoir.

FIG. 5 illustrates a close-up side view of a fluid distribution system 20 having a compressible fluid reservoir 28. The fluid reservoir 28 may be compressed in an engagement direction (E) to increase an internal pressure within the fluid reservoir 28 and force lubricant in a fluid direction (D) through a valve 14 and into a fluid line 22 to be distributed to one or more jaws of an electrosurgical device (D) (see FIG. 1). The fluid reservoir 28 may be refilled via a refill port 30 located at a distal end of the fluid reservoir 28.

Figure 6:
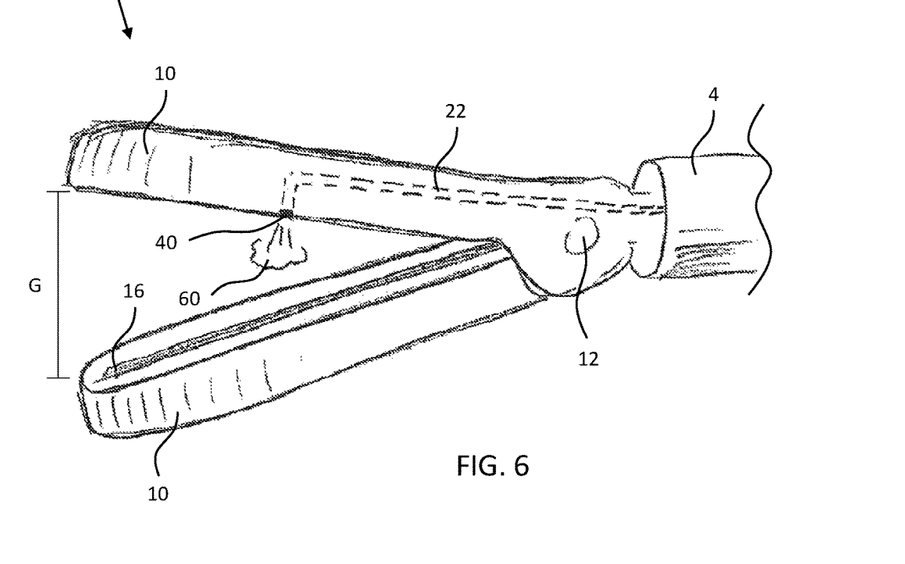
FIG. 6 is a close-up perspective view of an electrosurgical device with an integrated fluid line for dispensing a lubricant.

FIG. 6 illustrates a close-up perspective view of an electrosurgical device 2. The electrosurgical device 2 includes a surgical device 4 connected to a plurality of jaws 10. The jaws 10 are pivotally engaged about a pivot 12 so that the jaws 10 may open and close by increasing or decreasing a gap (G) between the jaws 10. A fluid distribution system (not shown) located in the surgical device 4 distributes a lubricant 60 through a fluid line 22 so that the lubricant 60 exits a fluid opening 40 and lubricates one or more surfaces of the jaws 10 (see FIG. 1). One or more of the jaws 10 includes a channel 16 that initially receives the lubricant 60 exiting the fluid opening 40 and gradually dispenses the lubricant 60 to the one or more surfaces of the jaws 10 (see FIG. 7).

Figure 7:
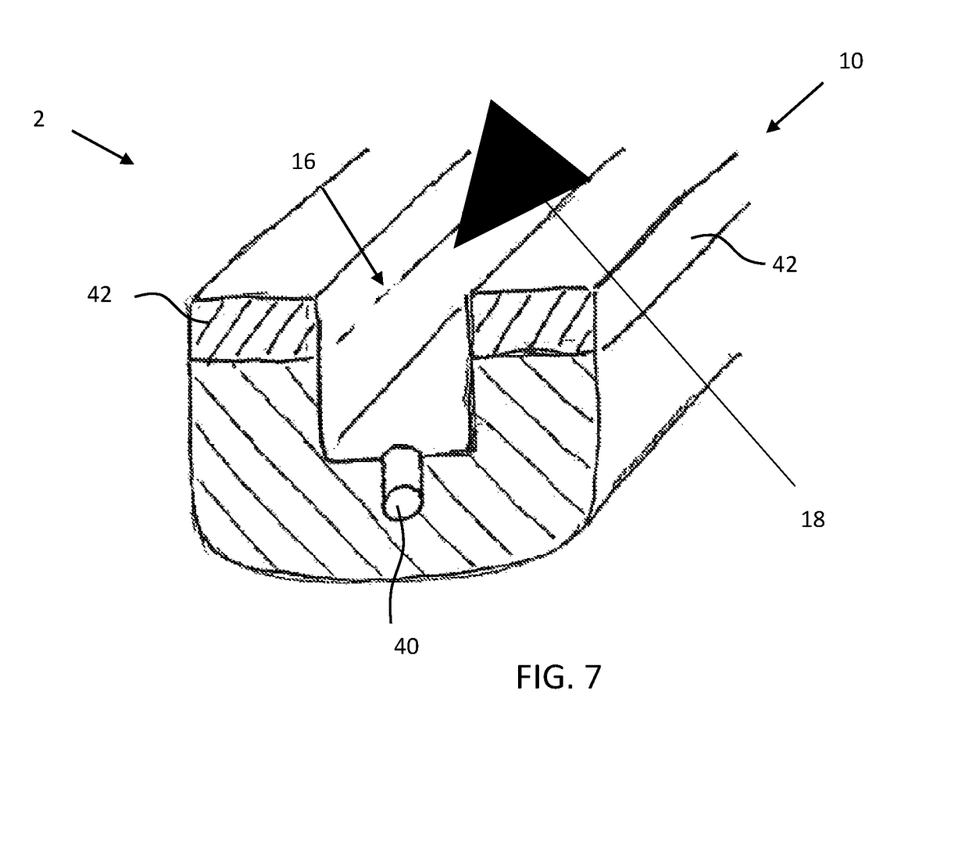
FIG. 7 is a cross-section of a jaw of an electrosurgical device.

FIG. 7 illustrates a cross-section of a jaw 10 of an electrosurgical device 2, including a blade 18. The jaw 10 includes a plurality of conduction plates 42 disposed on an outer surface that surround a central channel 16. A fluid opening 40 dispenses a lubricant flowing from a fluid distribution system (not shown) into the channel 16, whereby the channel 16 gradually dispenses the lubricant to lubricate the one or more conduction plates 42 (see FIG. 1).

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Electrosurgical Device
4 Surgical Device
12 Pivot
14 Valve
16 Channel
20 Fluid Distribution System
22 Fluid Line
24 Fluid Pump
26 Engagement Switch
28 Fluid Reservoir
30 Refill Port
32 Activation Device
34 Motor
36 Cam
40 Fluid Openings
42 Conduction Plate
44 Activation Switch
50 Power Supply/generator
52 Wire
60 Lubricant
62 Handle
64 Trigger
66 Neck
70 Mounting Portion
E Direction for Engagement
D Fluid Direction
R Direction of Rotation

We claim:
1. An electrosurgical instrument comprising:
   first and second opposing jaws each extending from a proximal end to a distal end and defining opposing tissue-engaging surfaces, the first and second jaws pivotally engaged about a pivot at the proximal ends and movable between an open position and a closed position;
   a reciprocating blade;
   a U-shaped channel in the first jaw for receiving the reciprocating blade such that at least a portion of the reciprocating blade extends through the channel, the channel extending longitudinally in a proximal-to-distal direction along a length of the first jaw and defined by first and second opposing channel side walls, a channel base wall recessed from the tissue-engaging surface of the first jaw, and a channel opening in the tissue-engaging surface of the first jaw, the channel base wall including a plurality of fluid openings distally spaced from the pivot for delivering a fluid directly into the channel; and a fluid distribution system in communication with the plurality of fluid openings for delivering the fluid to the channel;

wherein the electrosurgical instrument is configurable between a non-cutting state where the reciprocating blade remains retracted relative to the first and second jaws and a cutting state where the reciprocating blade reciprocates within the channel;

wherein the fluid distribution system is operable to selectively deliver the fluid to the channel to lubricate the opposing tissue-engaging surfaces of the first and second jaws when the electrosurgical instrument is in the non-cutting state; and wherein the fluid distribution system is operable to selectively deliver the fluid to the channel to lubricate the reciprocating blade when the el electrosurgical instrument is in the cutting state.

2. The electrosurgical instrument of claim 1, wherein the fluid distribution system includes one or more fluid lines that are connected to the plurality of fluid openings located within the channel.

3. The electrosurgical instrument of claim 2, wherein the fluid distribution system includes one or more fluid pumps and the one or more fluid lines are connected to the one or more fluid pumps, which pump the fluid through the one or more fluid lines and out of the plurality of fluid openings.

4. The electrosurgical instrument of claim 3, wherein the fluid distribution system includes one or more fluid reservoirs that are connected to the one or more fluid pumps that supply the fluid to the one or more fluid pumps.

5. The electrosurgical instrument of claim 4, wherein the one or more fluid reservoirs include one or more refill ports.

6. The electrosurgical instrument of claim 3, wherein the one or more pumps include an engagement switch that activates the one or more pumps so that the fluid is pumped into the channel.

7. The electrosurgical instrument of claim 6, wherein the engagement switch is in communication with an activation device, a cam, or both that assists in moving the engagement switch during operation of the one or more pumps.

8. The electrosurgical instrument of claim 7, wherein the activation device is movably supported by one or more mounting portions.

9. The electrosurgical instrument of claim 2, wherein the fluid distribution system includes one or more pumps that are connected to the one or more fluid lines and the one or more pumps include one or more fluid reservoirs.

10. The electrosurgical instrument of claim 9, wherein the one or more pumps are a syringe.

11. The electrosurgical instrument of claim 1, wherein the fluid distribution system includes one or more fluid lines that include one or more valves.

12. The electrosurgical instrument of claim 1, wherein the fluid is a bio-compatible anti-stick solution.

13. The electrosurgical instrument of claim 1, wherein the tissue-engaging surface of the first jaw comprises one or more conduction plates.

14. A method comprising:
pumping a lubricant from a fluid distribution system into a U-shaped channel located within a first jaw of an electrosurgical device that is pivotally engaged with a second jaw at a pivot, the pivot disposed at respective proximal ends of the first and second jaws, the electrosurgical device including a reciprocating blade that is operable to extend within the channel, the channel extending longitudinally in a proximal-to-distal direction along a length of the first jaw and defined by one or more channel walls recessed from a tissue-engaging surface of the first jaw and a channel opening in the tissue-engaging surface of the first jaw, the channel including a plurality of fluid openings in the one or more channel walls distally spaced from the pivot for delivering the lubricant directly into the channel, wherein the electrosurgical device is selectively configurable between a non-cutting state where the reciprocating blade remains retracted relative to the first and second jaws and a cutting state where the reciprocating blade reciprocates within the channel;

when the electrosurgical device is in the non-cutting state:
equally distributing the lubricant from the plurality of fluid openings through the channel and to the tissue-engaging surface of the first jaw; and when the electrosurgical device is in the cutting state:
filling the channel with the lubricant as the blade is advanced through the channel; and
reciprocating the blade repeatedly so that the lubricant within the channel coats the blade in the lubricant.

15. The method of claim 14, wherein the method includes a step of depressing an engagement switch into a fluid pump of the fluid distribution system to pump the lubricant into the channel.

16. The method of claim 14, wherein the method includes a step of transferring the lubricant from a fluid reservoir to a pump of the fluid distribution system.

17. The method of claim 14, wherein the method includes a step of rotating a cam to activate a pump of the fluid distribution system so that the lubricant is pumped into the channel.

18. The method of claim 14, wherein the method includes a step of contracting a fluid reservoir of the fluid distribution system so that the fluid distribution system acts as a pump and moves the lubricant into the channel.

19. The method of claim 14, wherein the method includes a step of metering a predetermined amount of the lubricant out each of the plurality of fluid openings.

20. The method of claim 14, wherein each one of the plurality of fluid openings defines a cross-sectional thickness that decreases between an entrance of the fluid opening and an exit of the fluid opening.

* * * * *